United States Patent [19]

Molday

[11] 4,452,773

[45] Jun. 5, 1984

[54] MAGNETIC IRON-DEXTRAN MICROSPHERES

[75] Inventor: Robert S. Molday, Vancouver, Canada

[73] Assignee: Canadian Patents and Development Limited, Canada

[21] Appl. No.: 365,562

[22] Filed: Apr. 5, 1982

[51] Int. Cl.³ .................... A61K 43/00; G01N 27/00; G01N 33/54; D06M 16/00

[52] U.S. Cl. .................................... 424/1.1; 436/526; 436/529; 436/530; 435/264; 210/632; 252/62.53; 252/62.54; 252/62.55; 424/9

[58] Field of Search ................. 424/1, 1.5; 436/526, 436/529, 530; 252/62.53, 62.54, 62.55; 210/632; 435/264

[56] References Cited

U.S. PATENT DOCUMENTS

| | | | |
|---|---|---|---|
| 3,720,760 | 3/1973 | Bennich et al. | 436/529 |
| 3,995,018 | 11/1976 | Stöquist | 424/1.5 |
| 4,018,886 | 4/1977 | Giaever | 436/526 |
| 4,070,246 | 1/1978 | Kennedy et al. | 252/62.54 |
| 4,101,435 | 7/1978 | Hasegawa et al. | 252/62.53 |
| 4,108,975 | 8/1978 | Hales | 436/529 |
| 4,115,534 | 9/1978 | Ithakission | 252/62.53 |
| 4,115,535 | 9/1978 | Giaever | 426/526 |
| 4,166,102 | 8/1979 | Johnson | 436/529 |
| 4,169,804 | 10/1979 | Yapel, Jr. | 252/62.54 |
| 4,177,253 | 12/1979 | Davies et al. | 436/526 |
| 4,278,651 | 7/1981 | Hales | 436/531 |
| 4,335,094 | 6/1982 | Mosbach | 424/1 |

OTHER PUBLICATIONS

Nye, Clin. Chim. ACTA, 69 (1976), 387–396.
Hersh et al., Clin. Chim. ACTA, 63 (1975), 69–72.

*Primary Examiner*—Christine M. Nucker
*Attorney, Agent, or Firm*—Wenderoth, Lind & Ponack

[57] ABSTRACT

The invention relates to colloidal sized particles composed of magnetic iron oxide ($Fe_3O_4$) coated with a polysaccharide, preferably dextran, or a derivative thereof having pendant functional groups. The particles have a magnetic moment, are electron dense, and are stable and non-aggregating under physiological conditions. They can be covalently bonded to antibodies, enzymes and other biological molecules and used to label and separate cells, cellular membranes and other biological particles and molecules by means of a magnetic field.

31 Claims, 6 Drawing Figures

MAGNETIC IRON-DEXTRAN MICROSPHERES

The present invention relates to colloidal sized particles composed of a magnetic iron oxide core coated with a water-soluble polysaacharide or a derivative thereof having pendant functional groups.

BACKGROUND OF THE INVENTION AND DISCUSSION OF THE PRIOR ART

Development of procedures for generating monoclonal antibodies against specific cells is described for instance in Köhler, G. and Milstein, C. (1975) "Continuous cultures of fused cells secreting antibody of predefined specificity", Nature 256, 495–497. These procedures have underlined the need to develop new and improved immunological labeling techniques to detect and separate specific cells. An approach initiated by the present inventor in collaboration with Dr. A. Rembaum and S.P.S. Yen and described in Molday, R.S., Yen, S.P.S. and Rembaum, A. (1977) "Application of magnetic microspheres in labeling and separation of cells, "Nature 268, 437–438 involved the synthesis of magnetic microspheres by cobalt γ-irradiation of iron oxide colloidal particles in the presence of hydrophilic and hydrophobic methacrylate monomers. These microspheres were coupled to immunoglobulin and used to label and separate cells by magnetic means. These magnetic reagents, however, were limited in application due to difficulties in synthesis and purification of the microspheres and, more important, susceptability to aggregation and nonspecific binding to certain types of cells. Kronick, P. L., Campbell, G., Joseph, K. (1978) "Magnetic microspheres prepared by redox polymerization used in a cell separation based on gangliosides", Science 200, 1074–1076 prepared similar magnetic polymeric particles, but these also appeared under the electron microscope as aggregated material on cell surfaces. Albumincoated microspheres have also been prepared for use as drug-carriers, Widder, K., Flouret, G. and Senyei, A. (1979) Magnetic microspheres: "Synthesis of a novel parenteral drug carrier", J. Pharm. Sci. 68, 79–82, but these reagents are relatively large in size, approximately 1 micron ($10^4$ Å) in diameter and, therefore, are limited as general reagents for cell labeling.

U.S. Pat. No. 3,970,518 of Giaever relates to the magnetic separation of biological particles such as cells, bacteria or viruses and makes use of magnetic particles coated with a layer of antibodies to the particles to be separated. The antibody coated magnetic particles contact a mixed population including the particles to be separated. The particles to be separated attach to the antibodies present on the magnetic particles, the magnetic particles are magnetically separated and the separated particles are subjected to a cleaving reaction to separate the required biological particles from the antibody-coated magnetic particles. The magnetic particles used can be ferromagnetic, ferrimagnetic or superparamagnetic. Suitable magnetic materials include oxides such as, for example, ferrites, perovskites, chromites and magnetoplumbites. The particles can range in size from colloidal to about 10 microns.

U.S. Pat. No. 4,018,886 of Giaever relates to a diagnostic method for determining the presence or absence of select proteins in low concentration in a liquid sample. A plurality of finely-divided magnetic particles, each of which is coated with a layer directly bonded thereto of first protein molecules specific to the select protein, is dispersed in the liquid sample. The select protein, if present attaches to the protein bonded to the magnetic particles. The magnetic particles are magnetically retrieved, washed and then treated with a cleaving agent solution in direct contact with a metallized surface. The select protein, if present, detaches from the protein-coated magnetic particles and attaches to the metallized surface, which is examined for presence of the select protein. The magnetic particles which are said to be useful are those useful in U.S. Pat. No. 3,970,518 and the size range for the particles is again colloidal to about 10 microns. In the only example use is made of nickel particles about 1 micron ($10^4$ Å) in diameter. Synthesis of these particles is difficult and the particles have been found to have a tendency to aggregation during protein coupling and cell labeling procedures.

U.S. Pat. No. 4,230,685 of Senyei et al. is concerned with magnetic separation of cells and the like and with microspheres for use therein. It discusses the teaching of U.S. Pat. No. 3,970,518 and says that there is no literature verification that uncoated magnetic particles can be made to bind effectively with antibodies. It refers to published procedures in which particles of magnetic material are contained in microspheres formed from polymers which can be coupled to antibodies. Mention is made of magnetically responsive microspheres formed from acrylate polymer, such as hydroxyethyl methacrylate, or polyacrylamide-agarose microspheres. Such microspheres can be chemically coupled to antibodies with glutaraldehyde or other di-aldehyde. One described procedure involves the chemical attachment of diaminoheptane spacer groups to the microspheres, which are then chemically linked to the antibodies by the glutaraldehyde reaction. Senyei et al state that although effective bonding of the antibodies can be obtained, such procedures are difficult since aggregation of microspheres can readily occur and the preparative procedure is time consuming. Further, random attachment of the antibodies to the magnetic particle means that that portion of the antibody which binds to the antigen, the Fab region, may not be available for binding. Senyei et al. propose to overcome these various disadvantages by using magnetically responsive microspheres having staphylococcal Protein A associated with the surfaces thereof. It is known that staphylococcal Protein A selectively binds to antibodies through the Fc region of the antibodies which is remote from the Fab region. Consequently the antibodies are arranged in oriented attachment with the Fab arms of the antibodies extending outwards. To attach the staphylococcal Protein A to the magnetic microspheres use is made of a polymer matrix material which does not mask the antibody binding sites of Protein A. The preferred matrix material is albumin but other materials mentioned are other amino acid polymers and synthetic polymers such as acrylate polymers. Examples mentioned are methyl methacrylate, hydroxyethyl methacrylate, methacrylic acid, ethylene glycol dimethacrylate, agarose polymers, polyacrylamide polymers or mixtures of such polymers. Albumin is the only polymer matrix material whose use is demonstrated in a working example. According to column 4 lines 24 to 27, the microspheres of Senyei et al. range in size from 0.2 to 100 microns (2000 to $10^6$ Å) in diameter preferably from about 0.5 to 2.0 microns (5000 to $2\times 10^4$ Å).

SUMMARY OF THE INVENTION

The present invention relates to colloidal sized particles of ferromagnetic iron oxide ($Fe_3O_4$) coated with a water-soluble polysaccharide or a reactive derivative thereof having pendant functional groups, and to a process for preparing such particles. The particles are prepared by mixing the water-soluble polysaccharide or a derivative thereof having pendant functional groups with an aqueous solution containing ferrous and ferric salts, adding alkali to the solution and separating polysaccharide- or polysacchride-derivative coated ferromagnetic iron oxide.

The particles of the invention have various useful properties. They can be readily mono-dispersed and are stable against aggregation and degradation under physiological conditions. They can be frozen and thawed without suffering adverse effects. As stated, they are colloidal in size and a diameter of about 100 to 700 Å, more particularly about 300 to about 400 Å is preferred, with an electron dense core of about 10 to 20 nm (100 to 200 Å). The particles have a magnetic moment and are electron dense so they can be used as visual markers in scanning and transmission electron microscopy. They are compatible with cells and other biological material and have functional reactive surface groups, i.e. the hydroxyl groups present in the saccharide moieties of the polysaccharide or functional groups derived from those hydroxyl groups. The particles are not themselves toxic and do not bond to cells nonspecifically. They can be bonded covalently to antibodies and to other biospecific molecules, for instance cells, enzymes, toxins, hormones, lectins, growth factors, nucleic acids, drugs and radioisotopes for use in a wide range of biomedical research studies and clinical procedures. In particular, they can be used to label specifically cells or other biological material. The properties of the particles permit separation of labeled cells or antigens either by means of a magnetic field or by centrifugation. The particles can be bonded to cytotoxic agents or drugs to serve as site-specific carriers for the agents or drugs, targeted by means of a magnetic field.

Thus, in one aspect the invention provides a method of labeling cells, enzymes, toxins, hormones, lectins, growth factors, nucleic acids or radioisotopes which comprises attaching to the cells, enzymes, toxins, hormones, lectins, growth factors, nucleic acids or radioisotopes colloidal sized particles of ferromagnetic iron oxide coated with a polysaccharide or a derivative thereof having pendant functional groups, the particles being attached to the cells, enzymes, toxins, hormones, lectins, growth factors, nucleic acids or radioisotopes via the functional group.

The particles of the invention have many applications in the field of medicine, as will be appreciated from the above. Their uses are not confined to the field of medicine, however. They can, for instance, be used in environmental research and operations. The particles can be coupled to proteolytic enzymes to be used to digest undesirable chemical agents. For example, cholera toxin can be digested with the enzyme pronase attached to particles of the invention. The particles are small enough to remain in suspension due to Brownian movement, but can readily be recaptured and concentrated using magnetic fields. In another aspect, therefore, the invention provides a method of cleaning water contaminated with an undesirable chemical agent which comprises adding to the water colloidal sized particles of ferromagnetic iron oxide coated with a polysaccharide or a derivative thereof having pendant functional groups to which is attached a proteolytic enzyme which will digest the undesirable chemical agent, and recovering the particles by magnetic means.

DESCRIPTION OF THE PREFERRED EMBODIMENTS

The water-soluble polysaccharide has pendant functional groups in the form of hydroxyl groups. These hydroxyl groups can be oxidized to aldehyde groups, and a preferred derivative of the polysaccharide is one containing aldehyde groups. It is not necessary that all the hydroxyl groups are oxidized to aldehyde groups. The aldehyde groups can be reacted with primary amine groups present on a molecule to form a Schiff base bonding the particle to the molecule to which the amine group is attached. To increase the stability of the bond it is preferred to subject the Schiff base to reduction. The preferred reducing agent is sodium borohydride but other reducing agents can of course be used.

The molecule bearing the primary amine group which reacts with the aldehyde group to form the Schiff base can be, for example, an antibody which is specific to a particular antigen. Particles of the invention to which the antibody is covalently bonded can be introduced into a population of antigens including the particular antigen to which the antibody is specific. There will be formed an antigen-antibody conjugate. This conjugate is attached to the ferromagnetic particles and so can be separated from other antigens by magnetic means. Subsequently the antigen-antibody conjugate can be dissociated to release the required antigen. Methods of dissociating the conjugate include reaction with sodium thiocyanate or urea, acidification, for example with formic acid, and digestion with a proteolytic enzyme such as trypsin.

The molecule bearing the primary amine group which reacts with the aldehyde to form the Schiff base can be an $\alpha,\omega$-alkylene diamine, for instance diaminoethane or diaminoheptane. Reaction to form a Schiff base, followed by reduction if required, results in a polysaccharide derivative having pendant amine groups. A wide variety of molecules including drugs, proteins, toxins, radio-isotope labeled compounds, fluorescent dyes, etc. can be bonded directly to amine groups or coupled to the amine groups using mild chemical agents and reactions, for example coupling with a dialdehyde such as glutaraldehyde. Further reaction with an $\alpha,\omega$-dialdehyde, for instance glutaraldehyde, forms Schiff base between the amine group attached to the polysaccharide and an aldehyde group of the dialdehyde. This produces a polysaccharide derivative which again has pendant aldehyde functional groups and which can react, for instance, with an amine group present on an antibody as described above.

The amino-containing molecule can be fluorescein isothiocyanate, which is a fluorescent dye.

The polysaccharide derivative can be one which contains cleavable bonds. Cleavage bonds can be introduced by reacting the polysaccharide with a bifunctional crosslinking agent, for example dimethyl 3,3'-dithiobispropionimidate, prior to reacting the polysaccharide with the molecule to which it is to be attached. When it is desired to spearate the polysaccharide from the molecule the cleavable bond is cleaved with a suitable reagent. In the case of dimethyl 3,3'-dithiobispropionimidate a disulfide bond is cleaved by addition of a reducing agent, for example 2-mercapto-ethanol.

By a water-soluble polysaccharide is meant a polysaccharide which will remain in solution in water at room temperature. Some polysaccharides, for instance agarose, can be dissolved in water with the aid of heat but on cooling form a gel. Such polysaccharides are considered not to be water-soluble and their use is not within the scope of this invention. Usually the polysaccharide has a molecular weight not greater than 70,000 and little crosslinking.

The water-soluble polysaccharides display hydrophilic properties which reduce or prevent any tendencies to aggregation of particles and nonspecific binding to cells and functional groups, and also have functional groups which are reactive, or can be rendered reactive, with proteins and other molecules. The preferred polysaccharide is dextran but other water-soluble polysaccharides can be used. Dextran is compatible with living organisms and is potentially biodegradable over long periods of time. The molecular weight of the water-soluble polysaccharide is not critical, although it will affect the size of the particles obtained. Satisfactory ferromagnetic polysaccharide microspheres have been made with dextran of molecular weight (Mav) of 10,000; 40,000 and 70,000. Polymers of mannose and sucrose and also derivatives of dextran have also been used successfully.

The particles of the invention can be readily and inexpensively prepared. An aqueous solution of a ferrous and a ferric salt is mixed with a solution of the polysaccharide or polysaccharide derivative. Alkali, suitably ammonium hydroxide or sodium hydroxide, is added to increase the pH and cause formation of magnetic iron oxide particles, to which the polysaccharide or polysaccharide derivative attaches. It will be appreciated that if use is made of a polysaccharide derivative containing aldehyde groups then ammonia cannot be used as the alkali which cause formation of the ferromagnetic iron oxide; the ammonia would react with the aldehyde groups. Solids can be separated by, for example, centrifugation and the polysaccharide-coated magnetic iron oxide particles separated from other soluble material by means of gel filtration chromatography on, for example, Sephacryl-300. (Sephacryl is a trademark of Pharmacia for beads of allyl dextran crosslinked with N,N'-methylene bisacrylamide with specified pore sizes).

The polysaccharide can be oxidized with, for example, sodium periodate and a preferred method of oxidation is a modification of the procedure used by Dutton, A. H., Tokuysau, K. T. and Singer S. J. (1979). "Iron-dextran antibody conjugates: General method for simultaneous staining of two components in high resolution immunoelectron microscopy,": Proc. Natl. Acad. Sci. United States of America 76, 3392. The sodium periodate partially oxidizes the carbohydrate residues of the polysaccharide residues. It is preferred to use a concentration of sodium periodate not greater than 5 mM when the particles are to be coupled with protein A, otherwise aggregation of the protein A-dextran iron oxide particles may possibly occur. The oxidation of the polysaccharide can be carried out before or after the formation of the magnetic iron oxide particles and the risk of aggregation is reduced if oxidation is carried out first. Although sodium periodate is the preferred oxidizing agent, other oxidizing agents which will convert glycol groups, as found in polysaccharides, to dialdehydes can be used, for example bromine and lead tetraacetate.

Ferromagnetic iron dextran particles in accordance with this invention have improved properties in comparison with previously developed polymeric magnetic microspheres which make them suitable for use in a wide variety of immunospecific cell labeling and separation applications. They are easily synthesized by reaction of ferrous chloride and ferric chloride with dextran or other polysaccharides under alkaline conditions and purified by conventional biochemical separation techniques. The particles are in an optimal size range for visualization of cell surfaces by scanning electron microscopy; see Molday, R. S. and Maher, P. (1980) "A review of cell surface markers and labeling techniques for scanning electron microscopy," Histochem. J. 12, 273-315, and contain an electron dense iron core which enables them to be seen in thin sections by transmission electron microscopy. When the particles are present on cell surfaces in sufficient density, they can be detected under the electron microscope on the basis of their iron content by X-ray microanalysis.

These ferromagnetic iron dextran particles, show relatively low levels of nonspecific binding to a variety of cells tested, including red blood cells, thymocytes, lymphocytes, myeloma tumor cells, neuroblastoma cells, photo-receptor cells, and do not aggregate in physiological buffer or during protein conjugation. It is hypothesized that this is due largely to the substantial dextran coating of 10-15 nm which surrounds the colloidal iron oxide core and endows the particles with an extremely hydrophilic surface, but the inventor does not wish to be bound by this hypothesis. Specific binding of the iron dextran particles to cell surfaces is achieved with surface specific ligands. Protein A has been coupled to ferromagnetic iron oxide dextran particles which have been oxidized under mild conditions with periodate. The Schiff base linkage produced between an aldehyde group of dextran and an amino group of Protein A was further stabilized to a secondary amine by borohydride reduction. Conjugates prepared by this procedure maintain their binding activity to Fc receptors of immunoglobulins and are stable against aggregation or dissociation even during freezing and thawing. A similar coupling procedure has been used by Dutton et al. above to conjugate immunoglobulin to Imposil particles (non-magnetic ferric oxyhydroxide-dextran particles). This procedure has been used to couple wheat germ agglutinin, as well as immunoglobulins, to ferromagnetic iron dextran particles and to label cells such as thymocytes and separate these cells from unlabeled cells.

An important feature of these iron dextran particles is their ferromagnetic properties. As we have shown, cells indirectly labeled with Protein A-ferromagnetic iron dextran particles were attracted to simple permanent magnets and separated from unlabeled cells. However, only cells which were heavily coated with the magnetic iron dextran reagents were quantitatively attracted to these magnets. When fewer particles are bound to cells, higher magnetic gradients are required. The high-gradient magnetic separation technique used by Melville, D., Paul, F. and Roath, S. (1975) "Direct magnetic separation of red cells from whole blood," Nature 255, 706. and Owens, C. (1978) "High-gradient magnetic separation of erythrocytes. Biophys. J. 22, 171-178," to remove paramagnetically-induced erythrocytes from blood, is valuable for the efficient, preparative magnetic separation of cells, cell membranes or receptors specifically labeled with ferromagnetic iron dextran particles. Owing to their dense property, these particles may also find application in separating out specific membrane fragments and vesicles in cell homogenate for biochemical studies.

The small ferromagnetic iron dextran reagents may find application in magnetic targeting of drugs such as vinblastine or ouabain or cytotoxic agents such as ricin or diphtheria toxin to specific tissues or tumors for diagnostic or therapeutic treatments. Immunospecific ferromagnetic iron dextran particles employing monoclonal antibodies may be particularly useful in such applications.

The invention is further illustrated with reference to the accompanying figures and the following experiments. The figures are briefly described as follows:

BRIEF DESCRIPTION OF THE DRAWINGS

FIG. 4(a) is a scanning electron micrograph and 4(b) a transmission electron micrograph of glutaraldehyde-fixed human red blood cells (RBC) sequentially treated with rabbit anti-human RBC serum and Protein A-ferromagnetic iron-dextran conjugate. FIG. 4(c) is a scanning electron micrograph and 4(d) a transmission electron micrograph of mouse thymocytes sequentially labeled with rabbit anti-mouse thymocyte antiserum and Protein A-ferromagnetic iron-dextran particles. FIGS. 4(e) and 4(f) are transmission electron micrographs of (e) a RBC and (f) mouse thymoctye treated only with Protein A-ferromagnetic iron-dextran particles.

Experimental Procedure

Figure 1:
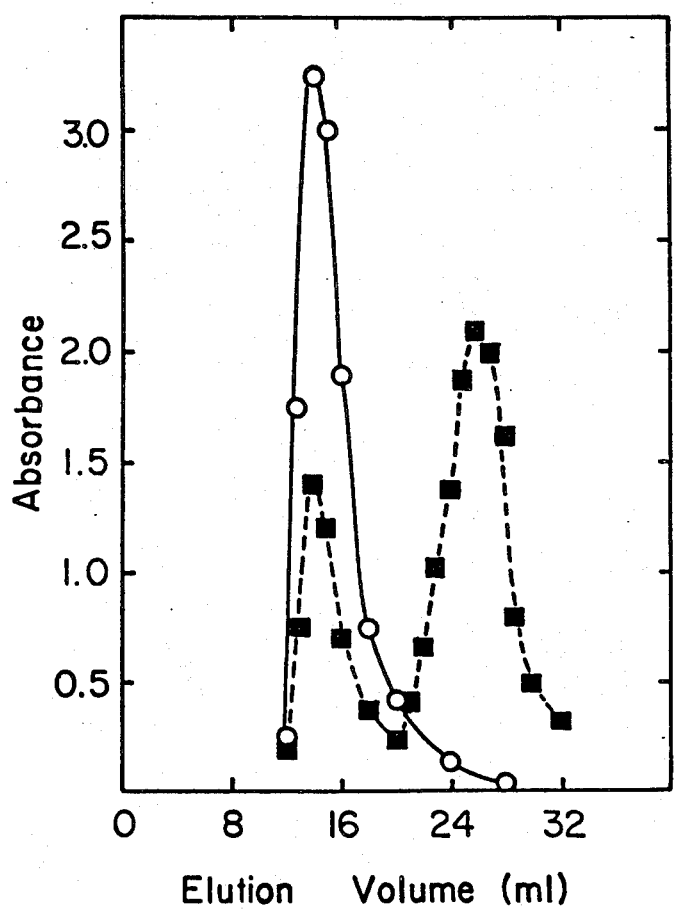
FIG. 1 is a graph of absorbance, measured in a spectrophotometer, against volume of aqueous buffer used in the separation of ferromagnetic-iron dextran particles from free dextran on a Sephacryl 300 column. Column eluate was assayed for iron (-0-) at 430 nm and for dextran (- ■ -) at 490 nm by the phenol/sulfuric acid method of Dubois, M., Gilles, K. A., Hamilton, J. K., Rebers, P. A. and Smith, F. (1956) Colorimetric Method for Determination of Sugars and Related Substances. Anal. Chem. 28, 350–356.

Synthesis of Magnetic Iron-Dextran Particles: Magnetic iron-dextran particles were prepared by mixing 10 ml of 50% (w/w) aqueous Dextran T-40 (Pharmacia) with an equal volume of an aqueous solution containing 1.51 g FeCl$_3$-6H$_2$O and 0.64 g FeCl$_2$-4H$_2$O. While stirring, the mixture was titrated to pH 10–11 by the dropwise addition of 7.5% (v/v) NH$_4$OH heated to 60°–65° C. in a water bath for 15 minutes. Aggregates were then removed by 3 cycles of centrifugation in a low-speed clinical centrifuge at 600 g for 5 minutes.

The ferromagnetic iron-dextran particles were separated from unbound dextran by gel filtration chromatography on Sephacryl-300. Five ml of the reaction mixture were applied to a 2.5×33 cm column and eluted with 0.1 M Na acetate 0.15 M NaCl at pH 6.5. The purified ferromagnetic iron-dextran particles collected in the void volume had a concentration of 7–10 mg/ml as determined by dry weight analysis.

Periodate Oxidation of Ferromagnetic Iron-Dextran: Periodate oxidation was carried out by a modification of the above-mentioned procedure used by Dutton et al. Routinely, 5 ml of iron-dextran particles at a concentration of 7–10 mg/ml were oxidized with 5 mM NaIO$_4$. After 60 min at 23° C., the iron-dextran solution was dialyzed overnight against 1 l of 20 mM sodium borate buffer pH 8.5 at 4° C., to remove excess periodate.

Preparation of Protein A-ferromagnetic Iron-Dextran Conjugates: The time course for the coupling of S. Aureus Protein A (Pharmacia) to iron-dextran particles was determined by reacting 75 $\mu$l of periodate-oxidized iron-dextran with 25 $\mu$l of 1 mg/ml $^{125}I$-Protein A ($4.64 \times 10^4$ cpm/$\mu$gm) in 20 mM sodium borate buffer pH 8.5 in 0.3 ml microtiter walls. The reaction was quenched at various times by the addition of 20 $\mu$l of 0.5 M glycine followed by reduction with 20 $\mu$l of 0.25 M NaBH$_4$.

The effect of protein concentration on the extent of coupling was studied by reacting 75 μl of oxidized ferromagnetic iron-dextran with 25 μl of 0.01–1.0 mg/ml $^{125}$I-Protein A at 23° C. for 8 hrs.

In these assays $^{125}$I-Protein A iron-dextran conjugates were separated from uncoupled $^{125}$I-Protein A by layering 100 μl of the reaction mixture onto 250 μl of 10% (w/w) BSA in 400 μl Eppendorf polypropylene microfuge tubes. After centrifugation for 60 min at 26,000 rpm in a Beckman SW-27 rotor, above, the bottom of the tubes containing the conjugate was cut with a hot scalpel and counted for $^{125}$I in a Beckman 8000 Gamma Counter.

For cell labeling Protein A-ferromagnetic iron-dextran conjugates were prepared by reacting 1.5 ml of oxidized ferromagnetic iron-dextran particles (7 mg/ml) with 0.15 ml of 5 mg/ml of Protein A in 20 mM sodium borate pH 8.5 at 23° C. for 8–12 hrs. The product was stabilized by reduction with 150 μl of 0.25 M NaBH$_4$ for 30 min. Unbound Protein A was separated from the conjugate by gel filtration chromatography on a 1.5×25 cm Sephacryl 300 column equilibrated with N-2-hydroxyethyl piperazine N'-2-ethanesulfonic acid (HEPES) buffer (20 mM HEPES, 0.15 M NaCl pH 7.4). The conjugate collected in the void volume was stored frozen in small vials at −20° C. at a concentration of 3–4 mg/ml.

For quantitative measurements, Protein A iron-dextran conjugates were labeled with $^{125}$I by the chloroamine T method (described by Hunter, W, M. and Greenwood, F. C. 91962) "Preparation of Iodine-131 labeled human growth hormone of high specific activity," Nature 194, 495–496. Approximately 1 μl of Protein A-iron-dextran conjugates (3–4 mg/ml) was reacted with 500 μCi of Na $^{125}$I (Amersham) and 100 μl of chloramine T (4 mg/ml) for 20 min at 22° C. The iodinated conjugate was then purified by chromatography on Sephacryl S-300 in HEPES buffer. The specific activity of the $^{125}$I-Protein A-iron-dextran conjugates was 4–12×10$^7$ cpm/mg.

Labeling of Cells: Human red blood cells were fixed with glutaraldehyde as by Molday, R. S., Dreyer, W. J., Rembaum, A. and Yen, S. P. S. (1975) "New immunolatex spheres: Visual markers of antigens or lymphocytes for scanning electron microscopy," J. Cell Biol. 64, 75–88. Thus, human red blood cells in phosphate buffered saline were fixed in 0.5% (v/v) glutaraldehyde for 60 min. at 25° C. and then washed in phosphate buffered saline by centrifugation. Mouse spleen lymphocytes were isolated by the Ficoll-isopaque method described by Böyum, A. (1968) "Isolation of leucocytes from human blood further observations," Scand. J. Clin. Lab. Invest. Suppl. 97 31. For cell labeling studies between 10$^6$ and 10$^7$ cells were treated with a saturating concentration of specific antiserum (rabbit antihuman RBC serum for RBC's or rabbit antithymocyte antiserum for thymocytes and lymphocytes) for 30–40 min at 23° C. The cells were then washed 3X with HEPES buffer containing 0.3% BSA by centrifugation (400 g×5 min) and resuspended in 50 μl of HEPES buffer. For quantitative binding studies 10 μl of cells (1×10$^6$ cells) were added to 50 μl of 0.5 mg/ml $^{125}$I-Protein A-ferromagnetic iron-dextran conjugates. Samples were incubated for 40–60 min at 23° C. after which the cells were layered on 0.2 ml of 10% (w/w) Ficoll 400 in 0.4 ml microfuge tubes and centrifuged in an Eppendorf Microcentrifuge Model 5413 for 3 min. The bottom of the tubes were then cut and counted as previously described. Samples were run in duplicate. In control experiments to test for the extent of nonspecific binding of $^{125}$I-Protein A-ferromagnetic iron-dextran conjugates to cells, the specific antiserum was substituted with buffer in the first labeling step.

Magnetic separation of labeled cells: For some quantitative measurements cells were initially tagged with $^{51}$Cr (20) at a specific activity of 3–4×10$^4$ cpm/10$^6$ cells. Cells were indirectly labeled with Protein A-ferromagnetic iron-dextran conjugates as described above. Separation of labeled from unlabeled cells were carried out by layering 10$^6$ cells 250 μl of HEPES buffer onto 0.8 ml of fetal calf serum in a 1.0 ml tuberculin syringe body fitted with a three way luer valve. The syringe was taped to one pole of a 19 lb. pull permanent horseshoe magnet (Eclipse) so that all the cells were in the magnetic field. After the specified time at 4° C., the syringe was gently eluted with 3 ml of HEPES buffer in order to collect the nonattracted cells. The syringe was then removed from the magnet and eluted with buffer. Additional cells which had been retained by the magnet were collected by centrifuging the syringe which had been placed in a tube at 600 g for 10 min. The number of magnetically attracted and nonattracted cells were determined by counting either $^{51}$Cr-tagged cells in a gamma counter or untagged cells in a hemocytometer.

Quantitative binding and magnetic attraction of human RBC labeled with $^{125}$I-Protein A iron-dextran conjugates. The effect of $^{125}$I-Protein A iron-dextran conjugate concentration on the extent of binding of the conjugate to cells and attraction of labeled cells to magnets was studied as follows. Ten μl of antibody labeled RBC (1×10$^6$ cells) were added to duplicate 50 μl samples of $^{125}$I-Protein A-iron-dextran (2×10$^5$ dpm/μg) serially diluted from 584 μg/ml to 4.5 μg/ml in HEPES buffer. After 60 min at 23° C. the individual samples were diluted with 325 μl of HEPES buffer. For quantitative binding studies, 125 μl of the samples were layered on 10%(w/w)Ficoll 400 in microfuge tubes and the separation of cells from unbound conjugate was carried out as described above. An additional 250 μl of sample was subjected to magnetophoresis as described.

Electron Microscopy: Cells indirectly labeled with Protein A-ferromagnetic iron-dextran conjugates were fixed with 1.25% glutaraldehydephosphate buffered saline, for 1 h, post-fixed in 1% osmium tetroxide, dehydrated in graded ethanol and either embedded in Epon* epoxy resin for transmission electron microscopy (TEM) or critical point dried from CO$_2$ and sputter-coated with gold-palladium for scanning electron microscopy (SEM) as previously described in the above-mentioned paper by Molday, Dreyer, Rembaum and Yen.

*Trademark

Results

Properties of Ferromagnetic Iron Dextran Particles

The reaction of ferrous chloride with ferric chloride under alkaline conditions in the presence of dextran polymers (Mav=40,000) yields a suspension of dextran coated ferromagnetic (Fe$_3$O$_4$) colloidal particles. Purification of these particles involves the removal of aggregated material produced during the reaction by low-speed centrifugation, and separation of unbound dextran from the ferromagnetic iron-dextran particles by gel filtration chromatography as shown in FIG. 1. Whereas these iron-dextran particles are excluded from Sephacryl S-300 and Sepharose 6B gel matrices, they are included and irreversibly trapped within Sepharose 4B and 2B beads. (Sepharose is a trademark for agarose-containing beads available from Pharmacia. Sepharose 6B is prepared with 6% agarose and has smaller pores than Sepharose 4B, prepared with 4% agarose, and Sepharose 2B prepared with 2% agarose.)

Purified ferromagnetic iron-dextran particles made in this manner contain about 50% Fe by weight relative to the particle dry weight. The iron micelle core is electron dense as visualized under the transmission electron microscope with a size ranging from 10-20 nm. Under the scanning electron microscope, the intact iron-dextran particles are roughly spherical in shape with a diameter of 30 to 40 nm. The iron-dextran particles are stable in physiological buffers and do not aggregate over a pH range of 3-10.

Iron-dextran particles prepared with dextran polymers of lower (Mav=10,000) and higher (Mav=70,000) molecular weights are also ferromagnetic and exhibit similar properties.

Protein A can be conjugated to the ferromagnetic iron-dextran particles by the periodate oxidation-borohydride reduction procedure previously used by Nakane and Kawaoi, Nakane, P. K. and Kawaoi, A. (1974) "Peroxidase-labeled antibody. A new method of conjugation." J. Histochem. Cytochem. 22, 1084–1091 in the preparation of immunoglobulin-horseradish peroxidase conjugates, and more recently, by Dutton, A. H., Tokuyasu, K. T. and Singer, S. J. (1979) "Iron-dextran antibody conjugates: General method for simultaneous staining of two components in high-resolution immunoelectron microscopy." Proc. Natl. Acad. Sci. U.S.A. 76, 3392 in the prepartion of immunoglobulin-Imposil conjugates. In the first step of this procedure, 5 mM sodium periodate was used to partially oxidize the carbohydrate residues of the iron-dextran particles. Higher periodate concentrations caused aggregation of subsequently prepared protein A-iron-dextran conjugates in physiological buffer.

Figure 2:
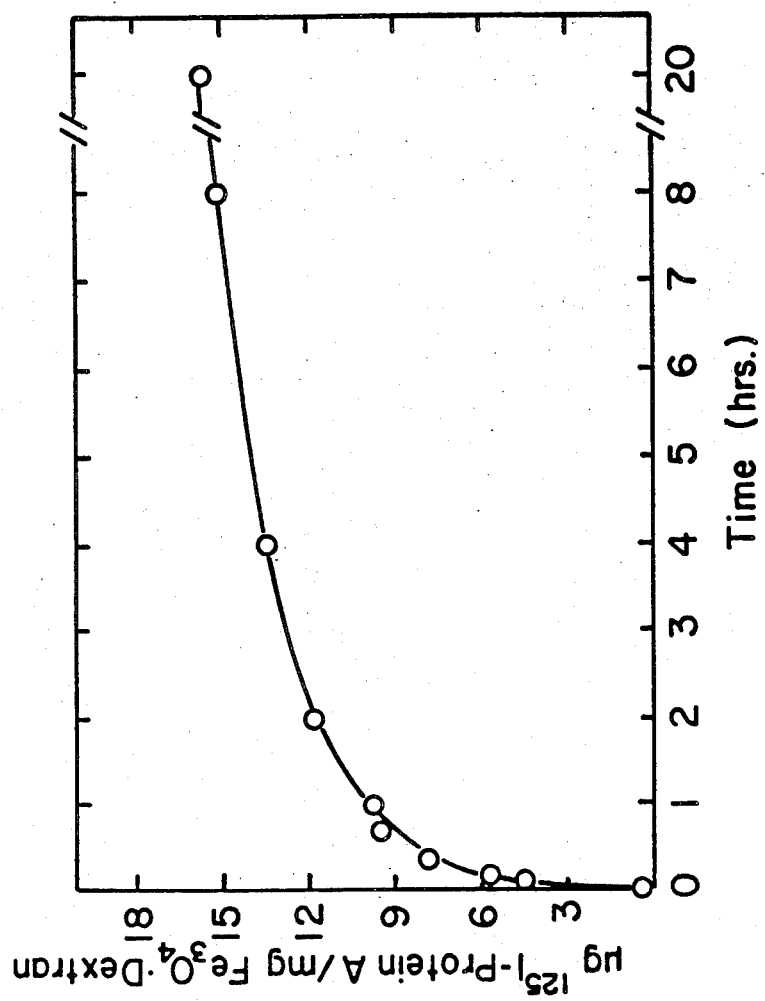
FIG. 2 is a graph of $\mu g$ of $^{125}I$-labeled Protein A per mg of ferromagnetic iron oxide dextran particles against time, to show the time course for the coupling of the Protein A to the ferromagnetic iron dextran particles. $^{125}I$-labeled Protein A (0.25 mg/ml, $4.6 \times 10^4$ cpm/mg) in 20 mM borate buffer pH 8.5 was reacted with periodate-oxidized iron dextran particles. The reaction was quenched at various times with 0.1 M glycine and 0.1% NaBH$_4$ and the conjugates were then separated from free $^{125}I$-labeled Protein A by centrifugation through 10% of Bovine serum albumin (BSA).
Figure 3:
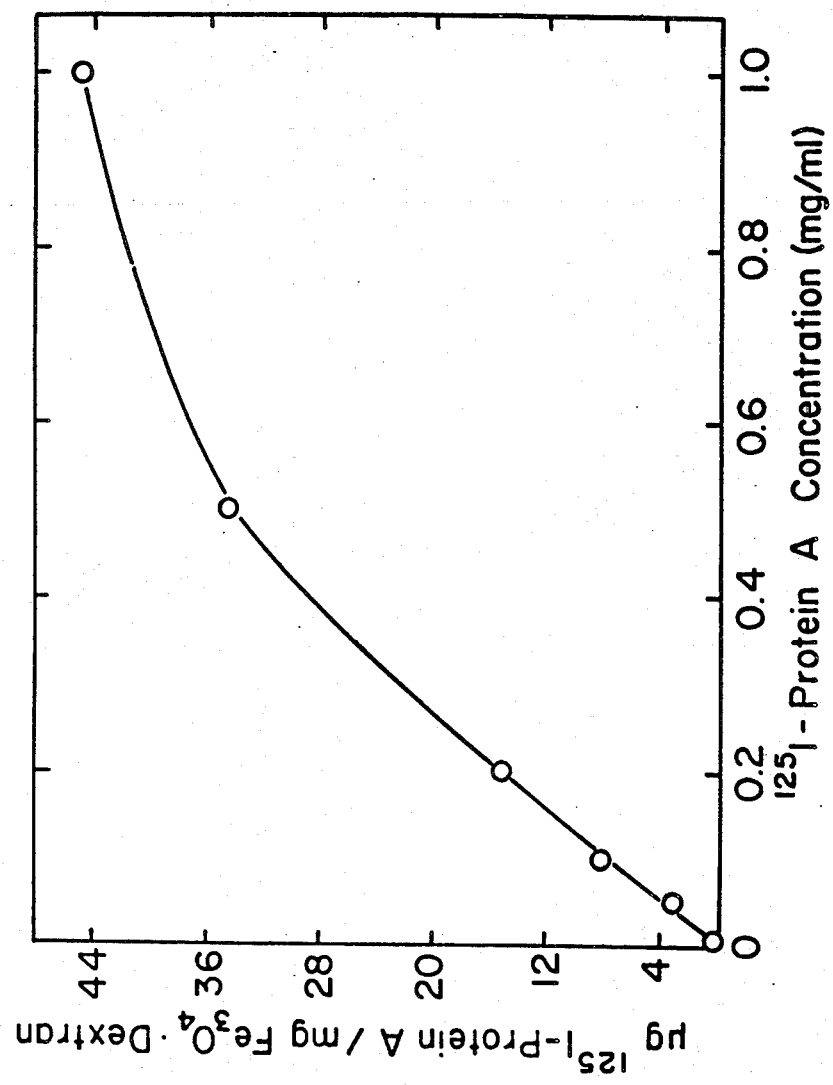
FIG. 3 is a graph of $\mu g$ of $^{125}I$-labeled Protein A per mg of ferromagnetic iron oxide dextran particles against time, to show the concentration dependence of Protein A coupling to ferromagnetic iron dextran. Various concentrations of $^{125}I$-Protein A in 20 mM borate buffer pH 8.5 were reacted with periodate-oxidized iron dextran for 8 hours at 22° C. The reaction was quenched and the conjugate was separated from free $^{125}I$-labeled Protein A by centrifugation through 10% BSA.

After removal of excess periodate by dialysis, the oxidized ferromagnetic iron-dextran particles were coupled to Protein A in the second step. The time course for the coupling of 0.25 mg/ml $^{125}$I-Protein A to the oxidized ferromagnetic particles is shown in FIG. 2. The reaction is 75% complete after 2 hours and over 90% complete after 8 hours. The effect of protein concentration on the extent of Protein A coupling to iron-dextran particles is illustrated in FIG. 3.

For cell labeling studies, protein A at 0.5 mg/ml was reacted with periodate-oxidized ferromagnetic iron-dextran particles for 8–12 hours. The conjugate was then stabilized by reduction with sodium borohydride and separated from free Protein A by gel filtration chromatography on Sephacryl S-300. Conjugates prepared by this procedure did not aggregate in physiological buffer and could be stored frozen indefinitely and subsequently thawed without significant aggregation or loss in binding activity.

Protein A was stably bonded to the ferromagnetic iron-dextran particles since no free protein A could be detected when the conjugate was rechromatographed on Sephacryl S 300 after storage for over a month.

Protein A-ferromagnetic iron-dextran conjugates as markers for SEM and TEM

Figure 4:
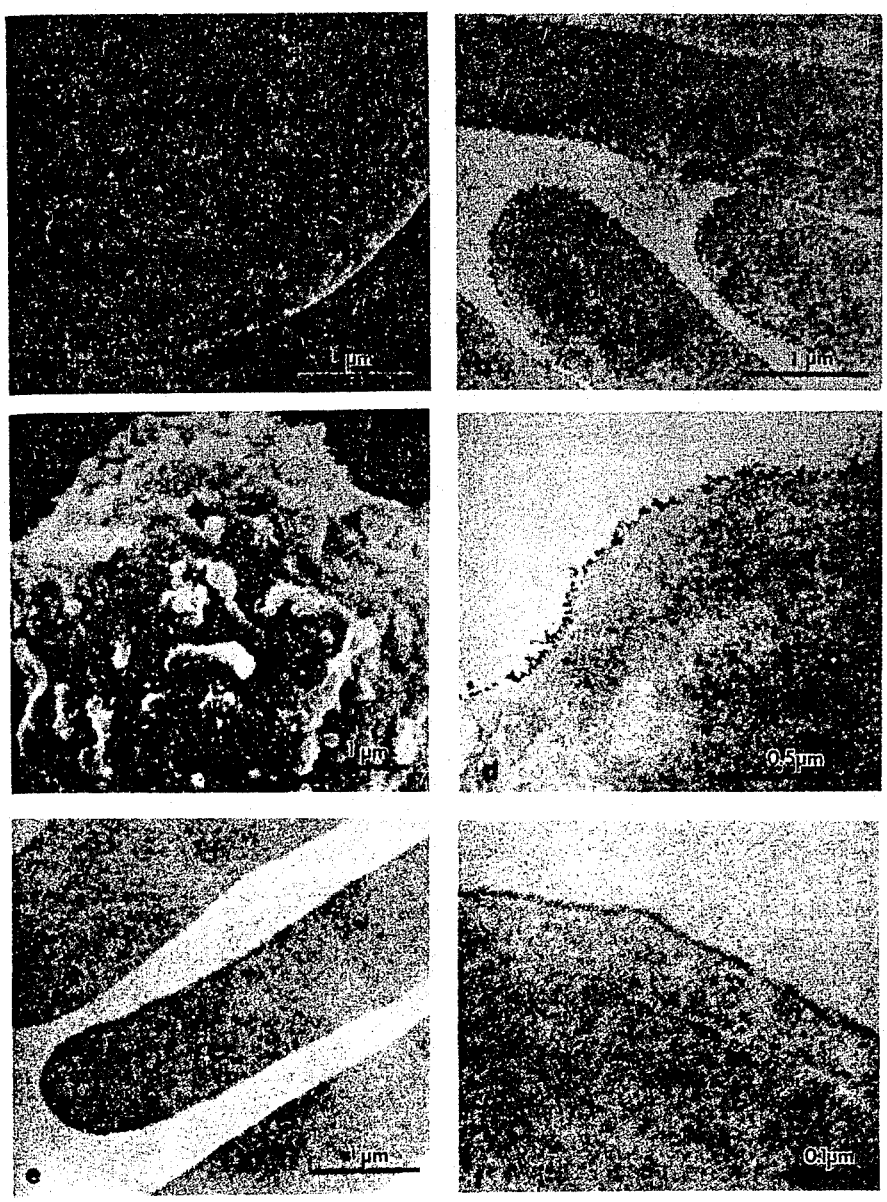
FIGS. 4(a) to 4(f) are electron micrographs illustrating use of ferromagnetic iron oxide dextran particles.

The application of Protein A-iron-dextran particles as visual markers for scanning and transmission electron microscopy is illustrated in FIG. 4. Glutaraldehyde-fixed human red blood cells and mouse thymocytes first treated with rabbit anti-red blood cell antiserum and rabbit anti-mouse thymocyte antiserum respectively and subsequently with Protein A-iron-dextran particles showed a dense, uniform pattern of surface labeling. In control experiments in which the primary cell specific antibody was omitted, no significant labeling was observed.

Quantitative Binding of Protein A-Iron-Dextran Particles to Cells

The specificity of binding of $^{125}$I-Protein A-Iron-dextran particles to antibody-treated and untreated cells is given in Table I.

TABLE I

| | | | |
|---|---|---|---|
| Binding of ($^{125}$I)-Protein A-Ferromagnetic Iron-Dextran Conjugates to Different Cell Types | | | |
| Cell Type | Primary Antibody | ($^{125}$I)-Protein A-$Fe_3O_4$ $DEX_{740}$ Conc. (mg/ml) | Amount Bound ($\mu g/10^8$ cells) |
| Glutaraldehyde fixed human erythrocytes | Rabbit αhRBC serum | 0.60 | 65.1 Test<br>3.1 Control |
| mouse thymocytes | Rabbit αmouse thymocyte serum | 0.97 | 117.7 Test<br>5.8 Control |
| mouse spleen lymphocytes | Rabbit αmouse thymocyte serum | 0.48 | 108 Test<br>12.8 Control |
| (Ficoll/Isopaque purified) | Rabbit αmouse IgG serum | 0.48 | 52.6 |

The apparent binding of $^{125}$I-Protein A-iron microspheres to fixed human red blood cells and unfixed thymocytes was approximately 5% of the binding to antibody treated cells. This value, however, may be an overestimation of nonspecific binding since it does not take into account the possible physical trapping of $^{125}$I-Protein A iron-dextran and sedimentation through the separation medium during centrifugation. Mouse spleen lymphocytes isolated on Ficoll-Isopaque gradient showed over 2-fold higher extent of apparent binding to cells. This may reflect the higher degree of nonspecific binding to certain cells in this relatively heterogeneous cell mixture.

Magnetic retention of cells labeled with Protein A-ferromagnetic iron-dextran conjugates When mouse spleen lymphocytes were sequentially labeled with anti thymocyte antiserum and Protein A-ferromagnetic iron-dextran particles and placed in a magnetic field, over 97% of the cells were retained by the magnet (Table II). Of these cells, 45% of the cells were eluted from the column after removal of the magnet, and the remaining cells were collected after centrifugation. In contrast, less than 12% of control cells i.e. cell treated only with Protein A-ferromagnetic iron dextran conjugates, were retained in the column. This retention, however, was independent of the presence of a magnetic field as indicated in Table II and therefore appeared to be due to adhesion of cells on the column walls.

TABLE II

Magnetic Retention of Cells Labeled with Protein A-Ferromagnetic Iron-Dextran Conjugates

| Cell Type | Primary Antibody | Cells loaded onto Magnets | Cells eluted (+ Magnet) | Cells eluted (− Magnet) | Residual recovered by centrifugation | |
|---|---|---|---|---|---|---|
| $^{51}$Cr-lymphocytes (Ficoll/Isopaque purified from mouse spleen) | Rabbit amouse thymocyte serum | $1.44 \times 10^6$ | $3.7 \times 10^4$ (2.6%) | $6.3 \times 10^5$ (44%) | $7.6 \times 10^5$ | Test |
| | | $1.23 \times 10^6$ | $1.0 \times 10^6$ (90%) | $5.5 \times 10^4$ (4.7%) | $7.0 \times 10^4$ (6.0%) | Control No Manipulation |
| | | $1.00 \times 10^6$ | $8.0 \times 10^5$ (89%) | $4.9 \times 10^4$ (5.4%) | $6.5 \times 10^4$ (6.2%) | Control plus RrA-F |

Figure 5:
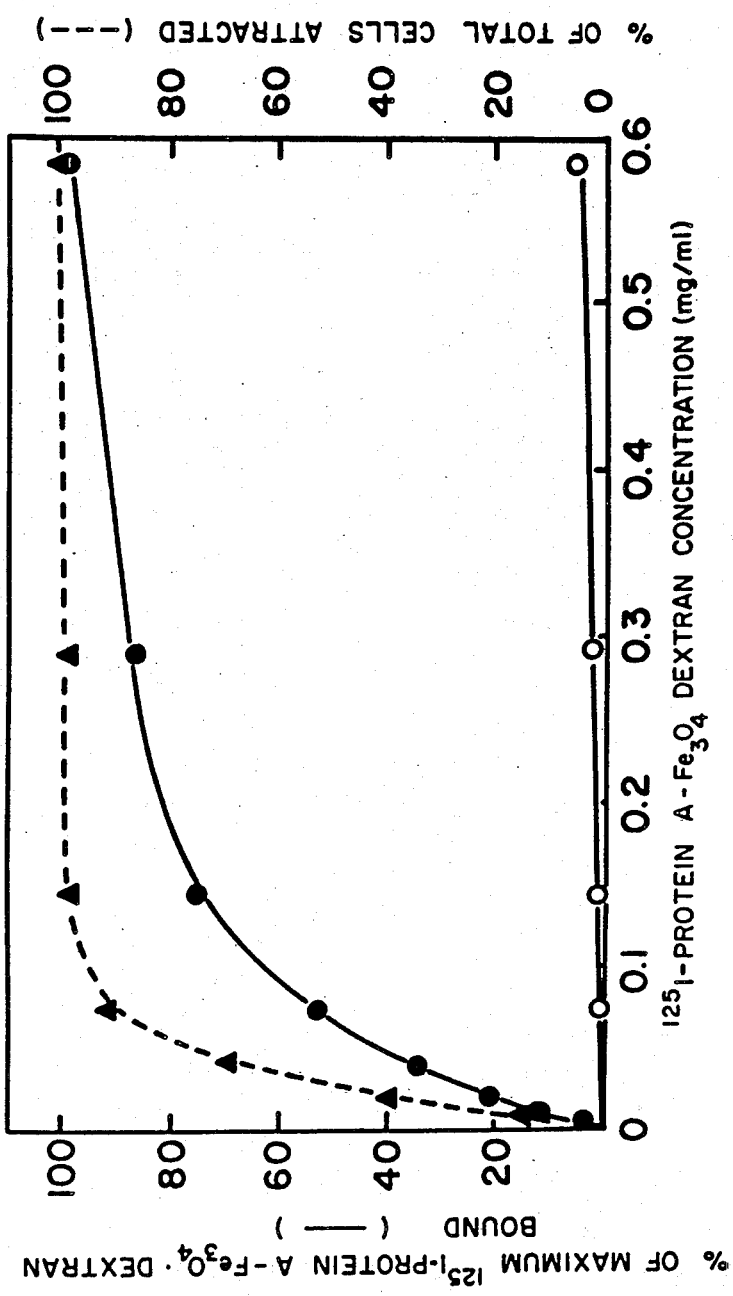
FIG. 5 is composed of three graphs showing the effect of Protein A-ferromagnetic iron-dextran conjugate concentration on extent of binding of conjugate to antibody-labeled human RBC and extent of attraction of labeled RBC to magnets. RBC's labeled with rabbit anti-human RBC antibodies were treated with various concentrations of $^{125}I$-Protein A-ferromagnetic iron-dextran conjugates (specific activity $2.0 \times 10^8$ dpm/mg) for 60 min at 4° C. The extent of binding (- ● -) was measured by sedimenting an aliquot of RBC through 10% Ficoll 400 and counting the pellet for $^{125}I$ in a gamma counter. Extent of binding to RBC which were not labeled with antibody (-0-) was run as controls to test for specificity of binding. Amount of RBC which were magnetically attracted was measured by layering aliquots of RBC treated with various concentrations of conjugates onto fetal calf serum in a 1 cc tuberculin syringe attached to one pole of a 19 lb. horseshoe magnet. After one hour at 4° C. the syringe column was eluted. After removing the syringe from the magnet the cells which had been retained by the magnet were collected by contrifugation (800 g×5 min) and counted in a hemo-cytometer (-- ▲ --).

The relationship between the extent of labeling of red blood cells with $^{125}$I-Protein A-iron-dextran conjugates and the extent of retention of these cells by the magnet is shown in FIG. 5. Over 90% of the labeled cells were attracted to the magnet during a 1 hour period when the cells were half-saturated with conjugates.

Figure 6:
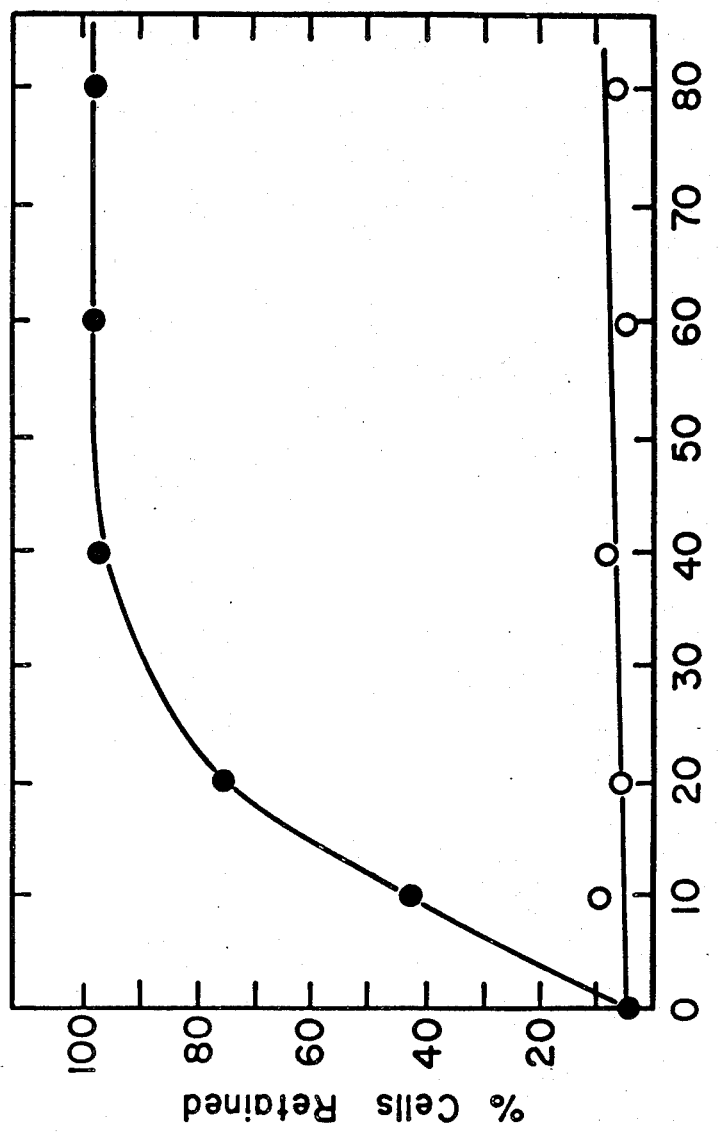
FIG. 6 is a graph showing magnetic separation of human red blood cells from mouse SP-2 cultured myeloma cells. Equal mixture of RBC and SP-2 cells were sequentially treated with rabbit anti-human RBC antiserum and Protein A-iron-dextran conjugates. The cells were then layered on fetal calf serum for 60 min in a syringe placed against a 19 lb. pull magnet. The syringe was eluted, removed from the magnet, and subjected to centrifugation. The number of RBC (- ● -) and SP-2 cells (-0-) recovered were determined by microscopic analysis.

Application of Protein A-iron-dextran conjugates in the Magnetic Separation of Cells The ferromagnetic property of Protein A-iron-dextran conjugates was used to separate by magnetic means labeled cells from unlabeled cells. When a mixture of mouse SP-2 cultured myeloma cells and red blood were sequentially labeled with anti-red blood cell antiserum and Protein A-iron-dextran conjugates and placed in a magnetic field, labeled red blood cells were retained by the magnet whereas over 95% of the SP-2 cells were not. The effect of time during which cells were maintained in the magnetic field on the separation of red blood cells from SP-2 cells is illustrated in FIG. 6. A small quantity of SP-2 cells was retained with the red blood cells, but this quantity did not increase with time and appears to be due to nonspecific adhesion of the cells to the column walls.

Preparation of diaminoethane-derivatized Dextran T-40

15 gms of Dextran T-40 was dissolved in 25 ml of 0.1M sodium acetate at pH 6.5. Sodium periodate (0.42 gms) was added with stirring for 30 min at 25° C. and the reaction was then dialyzed against 1 l of 0.01M Borate pH 8.6 to remove excess periodate.

The periodate-oxidized dextran was then reacted with 0.2M diaminoethane at pH 8.6 for 2 hrs at 25° C. The excess diaminoethane was removed by lyophilization.

Synthesis of diaminoethane-derivatized ferromagnetic iron-dextran microspheres

Synthesis was carried out by a similar procedure used to prepare underivatized ferromagnetic iron-dextran microspheres. Briefly, 50% w/w stock dextran consisted of 0.5 g diaminoethane-derivatized Dextran T-40 and 4.5 g of underivatized Dextran T-40 dissolved in 5 ml of water. To 5 ml of 50% stock dextran was added 5 ml of stock iron chloride solution consisting of 0.75 g $FeCl_3H_2O$ and 0.32 g $FeCl_2.4H_2O$. The mixture was stirred vigorously and then 10 ml of 7.5% $NH_4OH$ was added with stirring. The reaction was stirred at 25° C. for 1 hr. Aggregated material was removed by centrifugation and excess free dextran was separated out by gel filtration chromatography on Sephacryl S-300 as previously described.

Conjugation of goat anti-rabbit antibodies to diaminoethane-derivatized ferromagnetic iron-dextran microspheres Diaminoethane-derivatized iron-dextran microspheres were reacted with excess glutaraldehyde by adding 100 μl of 25% glutaraldehyde to 2 ml of the iron-dextran microspheres in 0.05M sodium phosphate buffer, pH 7. The mixture was stirred for 1 h at 25° C. and the excess glutaraldehyde was then removed by dialysis against 1 l of 0.01M sodium phosphate buffer pH 7. The goat antirabbit antibody was covalently bonded to the glutaraldehyde activated microspheres by adding 2 mg of antibody to 2 ml of the glutaraldehyde activated iron-dextran microspheres. The solution was stirred for 7 hours at 25° C. Protein A-ferromagnetic iron-dextran reagents were prepared in the same way.

Application of goat anti-rabbit antibody-ferromagnetic in dextran reagents

Red blood cells (RBC) sensitized with rabbit anti-RBC antibodies were treated with the goat antirabbit antibody-ferromagnetic iron-dextran reagents for 30 min at room temperature and subsequently washed by repeated centrifugation in phosphate-buffered saline. Electron microscopic analysis verified the presence of iron-dextran particles specifically attached to the RBC surface.

When the labeled RBC were passed through a column placed against a pole of an electromagnet, the RBC's were retained in the column by an applied magnetic field (10,000 gauss). Addition of stainless steel wire in the column increased the magnetic gradient and RBC labeled with the antibody-ferromagnetic iron-dextran could be quantitatively retained by application of a smaller magnetic field (2,000 gauss).

Persons skilled in the art will appreciate from the above the potential wide application of the invention in the use of immunospecific ferromagnetic iron oxide-dextran particles in specific cell labeling for electron microscopic analysis of antigen sites on cell surfaces and for separation of specific antigen bearing cells, cell membranes and receptors.

What is claimed is:

1. Discrete colloidal sized particles having a core of ferromagnetic iron oxide ($Fe_3O_4$) and coated with a water-soluble polysaccharide or a derivative thereof having pendant functional groups.

2. Particles as claimed in claim 1 having a diameter of about 100 to about 700 Å.

3. Particles as claimed in claim 1 having a diameter of about 300 to about 400 Å.

4. Particles as claimed in claim 1 wherein the polysaccharide is dextran.

5. Particles as claimed in claim 1 which have pendant aldehyde functional groups.

6. Particles as claimed in claim 1 which have pendant amino functional groups.

7. Particles as claimed in claim 1, 5 or 6 to which are attached biological molecules or particles bonded to functional groups of the polysaccharide or polysaccharide derivative.

8. Particles as claimed in claim 1 or 5 to which are attached a protein bonded to functional groups of the polysaccharide or polysaccharide derivative.

9. Particles as claimed in claim 5 to whose aldehyde functional groups is attached the protein *S. Aureus* Protein A.

10. Particles as claimed in claim 5 to whose aldehyde functional groups is attached immunoglobulin.

11. Particles as claimed in claim 1, 5 or 6 to which are attached biological molecules or particles selected from the group consisting of antibodies, cells, enzymes, drugs, toxins, hormones and nucleic acids.

12. Particles as claimed in claim 9 or 10 wherein there are attached to the protein biological particles selected from the group consisting of antibodies, cells, enzymes, drugs, toxins, hormones and nucleic acids.

13. A process for preparing colloidal sized particles as claimed in claim 1 which comprises mixing a water-soluble polysaccharide or a derivative thereof having pendant functional groups with an aqueous solution containing ferrous and ferric salts, adding alkali to the solution and separating polysaccharide- or polysaccharide derivative-coated ferromagnetic iron oxide particles.

14. A process according to claim 13 wherein the ferrous and ferric salts are ferrous and ferric chlorides.

15. A process according to claim 13 wherein aqueous ammonium hydroxide is added dropwise to the solution of ferrous and ferric salts to raise the pH to a value in the range of from 10 to 11.

16. A process according to claim 10 wherein the polysaccharide is dextran having an average molecular weight of between about 10,000 and about 70,000.

17. A process according to claim 13 wherein a polysaccharide at least some of whose hydroxyl groups have been oxidized to aldehyde group is mixed with the aqueous solution of ferrous and ferric salts, to obtain particles having pendant aldehyde functional groups.

18. A process according to claim 10 wherein a polysaccharide is mixed with the aqueous solution of ferrous and ferric salts and the process comprises the further step of oxidizing the polysaccharide coated particles to form pendant aldehyde functional groups.

19. A process according to claim 13 which comprises the further step of reacting a polysaccharide coated particle having pendant aldehyde functional groups with an amino-group containing molecule to form a Schiff base and then reducing the Schiff base so that the amino-group containing molecule is stably attached to the polysaccharide coated particle.

20. A process according to claim 19 wherein the amino-group containing molecule is a protein.

21. A process according to claim 20 wherein the protein is *S. Aureus* Protein A.

22. A process according to claim 20 wherein the protein is immunoglobulin.

23. A process according to claim 19 wherein the amino-group containing molecule is an α,ω-alkylene diamine and the process comprises the further step of reacting the obtained polysaccharide coated particles having pendant amino functional groups with an α,ω-dialdehyde, followed by reduction to obtain polysaccharide coated particles having pendant aldehyde groups.

24. A process according to claim 19 wherein the amino-group containing molecule is diaminoethane or diaminoheptane and the process comprises the further step of reacting the obtained polysaccharide coated particles having pendant amino functional groups with glutaraldehyde, followed by reduction to obtain polysaccharide coated particles having pendant aldehyde groups.

25. A process according to claim 13 which comprises the further step of reacting the product with biological particles selected from the group consisting of antibodies, cells, enzymes, drugs, toxins, hormones and nucleic acids.

26. A method of separating a required antigen from a population of antigens which comprises introducing into the population of antigens discrete colloidal sized particles having a core of ferromagnetic iron oxide and coated with a polysaccharide or a derivative thereof to which is attached an antibody specific to the required antigen, so that there are formed antigen-antibody conjugates on the particles, separating the particles by magnetic means and subsequently dissociating the antigen-antibody conjugate, to obtain the required antigen.

27. A method according to claim 26 wherein the antigen-antibody conjugate is dissociated by reaction with sodium thiocyanate, by reaction with urea, by acidification or by digestion with a proteolytic enzyme.

28. A method of treating a tumour which comprises introducing into the patient having the tumor a cytotoxic drug attached to discrete colloidal sized particles having a core of ferromagnetic iron oxide and coated with a polysaccharide and applying an external magnetic field to localize the particles bearing the cytotoxic drug in the region of the tumour.

29. A method of labeling cells, enzymes, toxins, hormones, lectins, growth factors, nucleic acids or radioisotopes, discrete colloidal sized particles having a core of ferromagnetic iron oxide and coated with a polysaccharide or a derivative thereof having pendant functional groups, the particles being attached to the cells, enzymes, toxins, hormones, lectins, growth factors, nucleic acids or radioisotopes via the functional group.

30. A method according to claim 29 which comprises the further step of separating labeled cells, enzymes, toxins, hormones, lectins, growth factors, nucleic acids or radioisotopes attached to the particles of ferromagnetic iron oxide by magnetic means.

31. A method of cleaning water contaminated with an undesirable chemical agent which comprises adding to the water discrete colloidal sized particles having a core of ferromagnetic iron oxide and coated with a polysaccharide or a derivative thereof having pendant functional groups to which is attached a proteolytic enzyme which will digest the undesirable chemical agent, and recovering the particles by magnetic means.

* * * * *